US012420042B2

United States Patent
Guo et al.

(10) Patent No.: US 12,420,042 B2
(45) Date of Patent: Sep. 23, 2025

(54) METHOD AND APPARATUS FOR EVALUATING AN AIRWAY STATUS

(71) Applicant: Shenzhen Mindray Bio-Medical Electronics Co., Ltd., Shenzhen (CN)

(72) Inventors: Jing Guo, Shenzhen (CN); Ruiling Pan, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 508 days.

(21) Appl. No.: 17/729,224

(22) Filed: Apr. 26, 2022

(65) Prior Publication Data

US 2022/0370744 A1 Nov. 24, 2022

Related U.S. Application Data

(63) Continuation of application No. 16/050,274, filed on Jul. 31, 2018, now Pat. No. 11,311,690, which is a
(Continued)

(51) Int. Cl.
*A61M 16/00* (2006.01)
*A61B 5/00* (2006.01)
(Continued)

(52) U.S. Cl.
CPC .......... *A61M 16/024* (2017.08); *A61B 5/08* (2013.01); *A61B 5/082* (2013.01); *A61B 5/087* (2013.01);
(Continued)

(58) Field of Classification Search
None
See application file for complete search history.

(56) References Cited

U.S. PATENT DOCUMENTS

| 8,371,303 | B2 | 2/2013 | Schaper |
| 2005/0284482 | A1 | 12/2005 | Patel |

(Continued)

FOREIGN PATENT DOCUMENTS

| CN | 101394886 A | 3/2009 |
| CN | 102264423 A | 11/2011 |

(Continued)

OTHER PUBLICATIONS

European Art 94(3) Opinion for EP 20217392.8 dated May 8, 2023.
Artime et al., "Tracheal Extubation," Respiratory Care, Jun. 2014, vol. 59, No. 6, pp. 991-1005.

*Primary Examiner* — Jay B Shah
(74) *Attorney, Agent, or Firm* — PV IP PC; Wei Te Chung

(57) ABSTRACT

An airway status evaluation apparatus includes a respiration monitoring unit, a data processing unit, an inflation/deflation unit, and an inflation/deflation control unit. The data processing unit is electrically connected to the respiration monitoring unit, collects a respiration parameter of a patient from the respiration monitoring unit when a cuff meets an evaluation state, and evaluates an airway status of the patient according to the respiration parameter. The inflation/deflation control unit is connected to the inflation/deflation unit and controls the inflation/deflation unit to inflate and deflate the cuff so as to enable the cuff to meet an evaluation state. In the present disclosure, inflation and deflation of the cuff are implemented in a full-automatic or semi-automatic control manner, the respiration parameter can be automatically monitored, and the evaluation result is automatically calculated, thereby achieving the automatic evaluation for the airway status of a patient.

9 Claims, 7 Drawing Sheets

Related U.S. Application Data continuation of application No. PCT/CN2016/074246, filed on Feb. 22, 2016.

(51) Int. Cl.
    *A61B 5/08*       (2006.01)
    *A61B 5/087*     (2006.01)
    *A61B 5/091*     (2006.01)
    *A61M 16/04*     (2006.01)
    *A61M 16/08*     (2006.01)

(52) U.S. Cl.
    CPC .............. *A61B 5/091* (2013.01); *A61B 5/743* (2013.01); *A61M 16/0003* (2014.02); *A61M 16/04* (2013.01); *A61M 16/044* (2013.01); *A61M 2016/0027* (2013.01); *A61M 16/0833* (2014.02); *A61M 16/0841* (2014.02); *A61M 2205/3592* (2013.01); *A61M 2205/502* (2013.01)

(56) References Cited

U.S. PATENT DOCUMENTS

| | | |
|---|---|---|
| 2008/0072913 A1 | 3/2008 | Baker et al. |
| 2009/0275805 A1 | 11/2009 | Lane |
| 2013/0281885 A1 | 10/2013 | Rowbottom |
| 2017/0188886 A1 | 7/2017 | Khemani |

FOREIGN PATENT DOCUMENTS

| | | |
|---|---|---|
| CN | 102770070 A | 11/2012 |
| CN | 104367325 A | 2/2015 |
| WO | WO 2013102905 A1 | 7/2013 |

METHOD AND APPARATUS FOR EVALUATING AN AIRWAY STATUS

CROSS-REFERENCE TO RELATED APPLICATIONS

This application is a continuation of U.S. application Ser. No. 16/050,274, filed Jul. 31, 2018, for METHOD AND APPARATUS FOR EVALUATING AN AIRWAY STATUS, which is a continuation of PCT Application No. PCT/CN2016/074246, filed Feb. 22, 2016, each of which is incorporated herein by reference.

TECHNICAL FIELD

The present disclosure relates to medical devices, and in particular to a method and apparatus for evaluating an airway status, as well as a ventilator including the apparatus.

BACKGROUND ART

Tracheal intubation involves the placement of a special endotracheal tube into the nasopharynx or oropharynx, transnasally or transorally, to establish an air passage in the trachea of a patient. Currently, tracheal intubation is a common and important first-aid technique and is an effective measure for ensuring that the patient's airway is unobstructed.

A conventional tracheal tube includes a catheter, an inflatable cuff, and an inflation tube. The catheter is placed into the trachea of the patient. When in use, an insertion end of the catheter is inserted into the trachea of the patient, an exposed end of the catheter is connected to a breathing circuit of a ventilator, and the cuff is fixed outside an end of the catheter inserted into the trachea. The cuff may fix the tube, close the trachea, and prevent an unwanted aspiration. The inflation tube is usually a long, thin flexible tube, with one end connected to an inside of the cuff, and the other end thereof exposed outside and connected to an inflation bag or a syringe. An operator may inflate the cuff by operating the inflation bag or the syringe.

Since the tracheal tube may be inserted into the trachea easily, it is commonly used in emergency situations. The tracheal tube is also convenient for sputum aspiration owing to the relatively large lumen, so it is often used in clinical contexts. However, establishing an artificial airway by tracheal intubation damages and destroys a normal physiological function of a body to some extent. For example, when the cuff pressure is excessively high, it is easy to cause airway damage due to insufficient blood supply to a tracheal mucosa of the patient. Moreover, long-term establishment of the artificial airway sometimes causes a tracheal stenosis of the patient. Therefore, before weaning and extubating for the patient, medical personnel need to evaluate the airway status of the patient and determine whether an extubation may be performed based on the airway patency, otherwise it would cause a difficulty in reintubation or even endanger the patient's life. Currently, the latest artificial airway cuff management guidelines also suggest that a cuff leak test should be performed to evaluate airway patency before extubation.

Conventionally, medical personnel evaluate the airway status based on experience, intubating the patient, operating the cuff, setting the ventilator, and observe the status of the patient. Because medical personnel have to do so many complicated operations, evaluation accuracy may decrease.

SUMMARY

An airway status evaluation apparatus may include: a respiration monitoring unit to monitor a respiration parameter of a patient; an inflation/deflation unit including an interface connected to an inflation tube of a tracheal tube, to inflate or deflate a cuff of the tracheal tube through the inflation tube; an inflation/deflation control unit, connected to the inflation/deflation unit, to control the inflation/deflation unit to inflate and deflate the cuff so as to enable the cuff to meet an evaluation state; and a data processing unit, electrically connected to the respiration monitoring unit, to collect the respiration parameter of the patient from the respiration monitoring unit when the cuff meets the evaluation state and to evaluate an airway status of the patient according to the respiration parameter.

An airway status evaluation apparatus may include: a respiration monitoring unit to monitor a respiration parameter of a patient; an inflation/deflation unit including an interface, connected to an inflation tube of a tracheal tube, to inflate or deflate a cuff of the tracheal tube through the inflation tube; a pressure sensor connected to the cuff to measure cuff pressure; an inflation/deflation control unit, electrically connected to a signal output end of the pressure sensor, to output a command or prompt information about inflating or deflating the cuff after an airway status evaluation procedure is started and to determine whether the cuff meets an evaluation state according to the cuff pressure; and a data processing unit, electrically connected to the respiration monitoring unit, to collect the respiration parameter of the patient from the respiration monitoring unit when the cuff meets the evaluation state and to evaluate an airway status of the patient according to the respiration parameter.

An airway status evaluation apparatus may include: an inflation/deflation unit including an interface, connected to an inflation tube of a tracheal tube, to inflate or deflate a cuff of the tracheal tube through the inflation tube; a pressure sensor connected to the cuff to measure cuff pressure; a connection unit to be in signal connection with a ventilator; and an inflation/deflation control unit, respectively electrically connected to the inflation/deflation unit and a signal output end of the pressure sensor, to control the inflation/deflation unit to inflate and deflate the cuff or output prompt information about inflating or deflating the cuff such that the cuff is inflated to a predetermined pressure or completely deflated, and further electrically connected to the connection unit and communicating with the ventilator through the connection unit so as to receive an inflation/deflation instruction from the ventilator and/or feed back the cuff pressure to the ventilator.

A ventilator may include: a breathing circuit, connected to an exposed end of a catheter of a tracheal tube, to provide a passage for a patient to inhale or exhale gas; a respiration unit to provide mechanical ventilation for the patient, the respiration unit being connected to the breathing circuit; and the airway status evaluation apparatus as any one described above, in which the respiration monitoring unit is connected to the breathing circuit to monitor respiration parameters of the patient.

An airway status evaluation method, using the airway status evaluation apparatus as described above to evaluate the airway status of a patient, may include: controlling the inflation/deflation unit to maintain the cuff at a predetermined pressure when the tracheal tube is in a normal ventilation mode; starting an airway status evaluation procedure based on an instruction from a user; controlling the respiration unit to provide mechanical ventilation at a preset tidal volume for a patient; acquiring a first respiration parameter of exhalation of the patient from a respiration monitoring unit when the cuff is at the predetermined pressure, and the first respiration parameter is a value measured in one respiratory cycle or an average value measured in multiple respiratory cycles; controlling the inflation/deflation unit to completely deflate the cuff; acquiring a second respiration parameter of exhalation of the patient from the respiration monitoring unit after the cuff is completely deflated, and the second respiration parameter is a value measured in one respiratory cycle or an average value measured in multiple respiratory cycles; and evaluating the airway status according to the first and second respiration parameters, and outputting an evaluation result.

An airway status evaluation method, using the airway status evaluation apparatus described above to evaluate the airway status of a patient, may include: controlling the inflation/deflation unit to maintain the cuff at a predetermined pressure when the tracheal tube is in a normal ventilation mode; starting an airway status evaluation procedure based on an instruction from a user; controlling the inflation/deflation unit to completely deflate the cuff; acquiring an inhalation parameter and an exhalation parameter of a patient from the respiration monitoring unit after the cuff is completely deflated, and the inhalation parameter and the exhalation parameter are values measured in one respiratory cycle or average values measured in multiple respiratory cycles; and evaluating the airway status according to the inhalation parameter and the exhalation parameter and outputting the evaluation result.

An airway status evaluation apparatus may include: a unit to control the inflation/deflation unit to maintain the cuff at a predetermined pressure when the tracheal tube is in a normal ventilation mode; a unit to start an airway status evaluation procedure based on an instruction from a user; a unit to control the respiration unit to provide mechanical ventilation at a preset tidal volume for a patient; a unit to acquire a first respiration parameter of exhalation of the patient from a respiration monitoring unit when the cuff is at the predetermined pressure, and the first respiration parameter is a value measured in one respiratory cycle or an average value measured in multiple respiratory cycles; a unit to control the inflation/deflation unit to completely deflate the cuff; a unit to acquire a second respiration parameter of exhalation of the patient from the respiration monitoring unit after the cuff is completely deflated, and the second respiration parameter is a value measured in one respiratory cycle or an average value measured in multiple respiratory cycles; and a unit to evaluate the airway status according to the first and second respiration parameters, and outputting an evaluation result.

An airway status evaluation apparatus may include: a unit to control the inflation/deflation unit to maintain the cuff at a predetermined pressure when the tracheal tube is in a normal ventilation mode; a unit to start an airway status evaluation procedure based on an instruction from a user; a unit to control the inflation/deflation unit to completely deflate the cuff; a unit to acquire an inhalation parameter and an exhalation parameter of a patient from the respiration monitoring unit after the cuff is completely deflated, and the inhalation parameter and the exhalation parameter are values measured in one respiratory cycle or average values measured in multiple respiratory cycles; and a unit to evaluate the airway status according to the inhalation parameter and the exhalation parameter and outputting the evaluation result.

A tracheal intubation device may include: a tracheal tube including a catheter, a cuff, and an inflation tube, the cuff surrounding an outer face of an end of the catheter, and the inflation tube having one end connected to the inside of the cuff, and the other end used to introduce air; and the airway status evaluation apparatus as described above, with the interface of the inflation/deflation unit being connected to the other end of the inflation tube.

One embodiment provides an airway status evaluation method, including: receiving an airway status evaluation instruction from a user; measuring an exhalation parameter of a patient when the cuff of an air tube is respectively in an inflated state and in a deflated state; comparing the exhalation parameter values measured respectively in the inflated state and in the deflated state; and outputting an airway status evaluation prompt according to the comparison result.

An airway status evaluation method may include: receiving an airway status evaluation instruction from a user; measuring an inhalation parameter value and an exhalation parameter value of a patient when the cuff of the air tube is in a deflated state; comparing the measured inhalation parameter value and the measured exhalation parameter value; and outputting an airway status evaluation prompt according to the comparison result.

An airway status evaluation apparatus may include: a receiving unit to receive an airway status evaluation instruction from a user and output an evaluation trigger command; a respiration parameter detection unit, connected to the interface unit, to measure exhalation parameters of a patient when the cuff of the air tube is respectively in an inflated state and in a deflated state after receiving the evaluation trigger command; a respiration parameter comparison unit, connected to the respiration parameter detection unit, to compare the exhalation parameter values measured respectively in the inflated state and in the deflated state; and an evaluation unit, connected to the respiration parameter comparison unit, to give a prompt to output an airway status evaluation prompt according to the comparison result.

An airway status evaluation apparatus may include: a receiving unit to receive an airway status evaluation instruction from a user and output an evaluation trigger command; a respiration parameter detection unit, connected to the interface unit, to measure an inhalation parameter value and an exhalation parameter value of a patient when the cuff of the air tube is in a deflated state after receiving the evaluation trigger command; a respiration parameter comparison unit, connected to the respiration parameter detection unit, to compare the measured inhalation parameter value and the measured exhalation parameter value; and an evaluation unit, connected to the respiration parameter comparison unit, to give a prompt to output an airway status evaluation prompt according to the comparison result.

DETAILED DESCRIPTION

Figure 1:
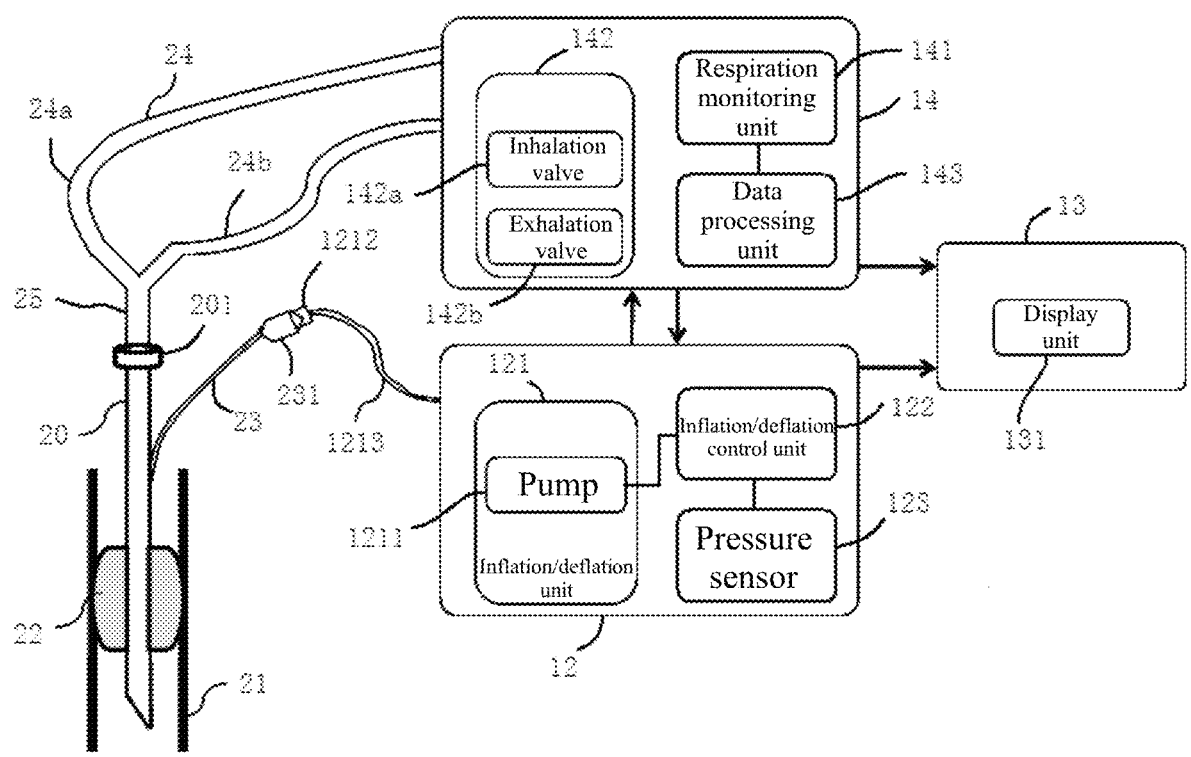
FIG. 1 is a schematic structural diagram of an airway status evaluation apparatus according to some embodiments.

In one embodiment, as shown in FIG. 1, a catheter 20 of a tracheal tube is placed into an airway 21 of a patient in a normal working state, a cuff 22 is fixed outside an end of the catheter 20 inserted into the airway 21, one end of an inflation tube 23 is connected to an inside of the cuff 22, and the other end thereof is exposed and is connected to an inflation/deflation unit. The inflation/deflation unit, as well as the other units described herein, may be implemented using hardware or by a processor executing instructions stored in a memory. An exposed end 201 of the catheter 20 is connected to a breathing circuit of a ventilator 24. In one embodiment, the breathing circuit 24 includes an inspiration conduit 24a and an expiration conduit 24b, and in illustrated example, the inspiration conduit 24a and the expiration conduit 24b are respectively connected to the exposed end 201 of the catheter of the tracheal tube through a Y-shaped member 25.

As previously noted, it is clinically necessary to evaluate an airway status of a patient before weaning the patient from the ventilator. In this embodiment, an airway status evaluation apparatus may include three units. A first unit 14 may include a respiration unit 142, a respiration monitoring unit 141, and a data processing unit 143, such as a CPU or the like. A second unit 12 may include an inflation/deflation unit 121 and an inflation/deflation control unit 122. A third unit may be an evaluation result output unit 13. In addition, the second unit 12 may further comprise a pressure sensor 123.

The respiration unit 142 may be connected to the breathing circuit 24, and may provide mechanical ventilation for the patient. In one embodiment, the respiration unit 142 may include an inhalation valve 142a and an exhalation valve 142b, an air flow flowing through the breathing circuit 24 may be controlled by opening/closing the inhalation valve 142a and the exhalation valve 142b to a certain degree, such that a specific air flow is output to a lung of the patient through the breathing circuit 24 and the catheter 20, and an airway pressure and a tidal volume may be maintained at a specific level, so as to implement mechanical ventilation for the patient.

The respiration monitoring unit 141 may monitor a respiration parameter of a patient. In one embodiment, the respiration monitoring unit 141 may monitor at least one respiration parameter, such as a tidal volume, a respiratory flow rate, an airway pressure, a carbon dioxide content, a chemical indicator content, and so on. In this embodiment, the respiration monitoring unit 141 may include a flow sensor. The respiration monitoring unit 141 may monitor a respiratory flow rate of the patient and output the respiratory flow rate to the data processing unit 143. The respiration monitoring unit 141 may be connected to the breathing circuit 24. For example, when the exposed end 201 of the catheter 20 is connected to the breathing circuit 24 of the ventilator through the Y-shaped member 25, the respiration monitoring unit 141 may be disposed in a channel of the Y-shaped member 25, and when the respiration monitoring unit 141 needs to respectively monitor respiration parameters of an expiratory phase and an inspiratory phase, the respiration monitoring unit 141 may be respectively connected to the inspiration conduit 24a and the expiration conduit 24b of the breathing circuit 24.

The data processing unit 143, electrically connected to the respiration monitoring unit 141, may collect the respiration parameters of the patient from the respiration monitoring unit 141 when the cuff meets an evaluation state and evaluate the airway status of the patient according to the respiration parameters.

The inflation/deflation unit 121 inflates the cuff 22 of the tracheal tube or deflates the cuff 22 through the inflation tube 23, the inflation/deflation unit 121 includes an air pump 1211 and a first interface 1212, and the first interface 1212 may be connected to an air input/output port of the air pump 1211 through a connecting tube 1213. Correspondingly, an exposed end of the inflation tube 23 of the cuff includes a second interface 231, and the second interface 231 may be fitted to the first interface 1212 to implement an airtight connection. After the second interface 231 is connected to the first interface 1212, an air passage is formed from the air pump 1211, through the connecting tube 1213, the first interface 1212, the second interface 231 and the inflation tube 23, and to the cuff 22. In one embodiment, the air pump 1211 may be replaced with a syringe, a proportional valve or an air evacuation valve, a power component of the syringe, the proportional valve or the air evacuation valve is electrically connected to the inflation/deflation control unit 122, and the air input/output port is connected to the first interface 1212 through the connecting tube 1213.

In this embodiment, the inflation/deflation control unit 122 is connected to the inflation/deflation unit 121, and is used to control the inflation/deflation unit 121 to inflate and deflate the cuff, so as to enable the cuff to meet an evaluation state. The required cuff evaluation state is different according to different evaluation standards. For some evaluation standards, the respiration parameters detected before and after cuff deflation are compared to make a determination, and therefore the cuff evaluation state required therefor refers to a state in which the cuff is inflated to a predetermined pressure before deflation and a state in which the cuff is completely deflated. For some evaluation standards, the respiration parameters of an inspiratory phase and an expiratory phase after cuff deflation are compared to make a determination, and therefore the cuff evaluation state required therefor refers to a state in which the cuff is completely deflated. In this embodiment, the connection method between the inflation/deflation control unit 122 and the inflation/deflation unit 121 may be electrical connection or may be mechanical or airway connection. In this embodiment, the inflation/deflation unit 121 is in an air pump manner, the inflation/deflation control unit 122 is electrically connected to the air pump to control the start and turning of the air pump so as to implement the inflation and deflation of the cuff.

The pressure sensor 123 is disposed on the inflation/deflation unit 121, and is used to measure the pressure of the cuff 22 after the inflation/deflation unit 121 is connected to the inflation tube 23. For example, the pressure sensor 123 is mounted on the air input/output port of the air pump through a mounting hole, or is mounted on the connecting tube 1213, or is mounted on the first interface 1212, such that the pressure sensor 123 may be connected to an air flow channel of the cuff 22. A signal output end of the pressure sensor 123 is electrically connected to the inflation/deflation control unit 122, and feeds back the pressure of the cuff 22 to the inflation/deflation control unit 122. The pressure sensor 123 is used to detect the cuff pressure. It is only an example that the pressure sensor is disposed on the inflation/deflation unit, and a person skilled in the art should understand that the pressure sensor may further be mounted in other ways, provided that the pressure sensor may be connected to the cuff when in use.

An evaluation result obtained by the data processing unit 143 may be output through the evaluation result output unit 13, and may be output via a sound, light, text image, or like manner. In one embodiment, the evaluation result output unit 13 includes a display unit 131, and the evaluation result obtained by the data processing unit 143 is displayed in graphically by the display unit 131. On the other hand, the display unit 131 may further receive parameters and instructions input by a user, after which the respiration unit 142 provides the preset mechanical ventilation according to the parameters input by the user, and the inflation/deflation control unit 122 controls the inflation/deflation unit 121 to inflate or deflate the cuff 22 based on the instructions input by the user. The inflation/deflation control unit 122 may further display the detected cuff pressure through the display unit 131.

Airway status evaluation processes according to two evaluation standards are respectively described below. During the specific description, an example is taken with tidal volume as the respiration parameter, but a person skilled in the art should understand that, in other embodiments, the respiration parameter used to evaluate the airway status may different, e.g., respiratory flow rate, airway pressure, carbon dioxide content, chemical indicator content, or the like.

Figure 2:
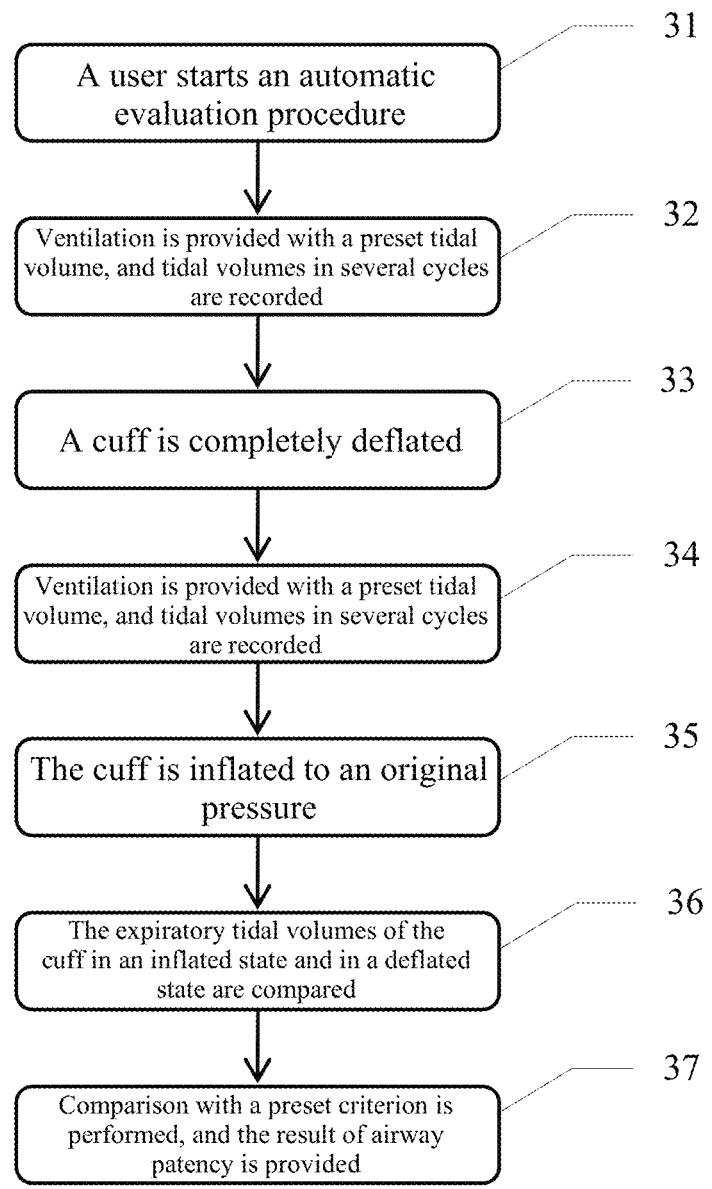
FIG. 2 is a schematic flowchart of an airway status evaluation method using respiration parameters detected before and after a cuff is deflated.

FIG. 2 shows an evaluation procedure according to the evaluation standard in which tidal volumes detected before and after cuff deflation are compared to make a determination, including the following steps.

In step 31, an airway status evaluation procedure is started. When the tracheal tube is in a normal ventilation mode, the inflation/deflation control unit controls the inflation/deflation unit to maintain the cuff at the predetermined pressure, and when it is needed to evaluate the airway status, a user (for example, a doctor or nurse) may input an instruction of starting the airway status evaluation procedure by means of the display unit or another trigger unit, so as to start an automatic airway status evaluation procedure. After the automatic airway status evaluation procedure is started, medical personnel may input on an interface the ventilation tidal volume and the number of respiratory cycles for measurement, or may use the default tidal volume and number of cycles.

In step 32, the respiration unit is controlled to provide mechanical ventilation for a patient with the preset tidal volume, and the expiratory tidal volume before deflation is recorded. At the depicted moment, the cuff is under the predetermined pressure and meets the evaluation state. When the respiration monitoring unit is a flow sensor, the flow sensor may monitor the respiratory flow rate of the patient in real time, the data processing unit may calculate the expiratory tidal volume according to the respiratory flow rate and save the expiratory tidal volume as a first respiration parameter, and the expiratory tidal volume before deflation may be a value measured in one respiratory cycle or an average value measured in multiple respiratory cycles, each respiratory cycle including an inspiratory phase and an expiratory phase.

In step 33, the inflation/deflation unit is controlled to completely deflate the cuff. After the expiratory tidal volume is recorded, the inflation/deflation control unit controls the inflation/deflation unit to deflate the cuff, the pressure sensor may monitor the pressure in the cuff in real time and feeds back the pressure in the cuff to the inflation/deflation control unit, and when the pressure in the cuff is less than a certain value (that is, when the cuff is completely deflated), the inflation/deflation control unit controls the inflation/deflation unit to stop deflation. At the depicted moment, the cuff is in a completely deflated state and meets the evaluation state.

In step 34, the expiratory tidal volume after deflation is recorded. The expiratory flow rate of the patient after the cuff is completely deflated is acquired from the respiration monitoring unit, the data processing unit may calculate the expiratory tidal volume according to the respiratory flow rate and save the expiratory tidal volume as a second respiration parameter, and the expiratory tidal volume after deflation may also be a value measured in one respiratory cycle or an average value measured in multiple respiratory cycles.

In step 35, the inflation/deflation unit is controlled to inflate the cuff to the preset pressure. After the tidal volume is collected, the cuff is inflated to the preset pressure, so as to enable the patient to be in the normal ventilation mode.

In step 36, the expiratory tidal volumes before and after deflation are compared. The comparison result may be the difference, ratio, percentage or the like between the expiratory tidal volumes before and after deflation.

In step 37, the comparison result is compared with the preset criterion to obtain the evaluation result of airway patency and output the evaluation result.

The evaluation process and the evaluation result may be displayed in a visualized manner through the display unit. For example, the data processing unit generates graphic data for displaying a visualized graph of a pharynx of the patient inserted by the tracheal tube and outputs the graphic data to the display unit, the display interface as shown in FIGS. 3-6, as described below.

Figure 3:
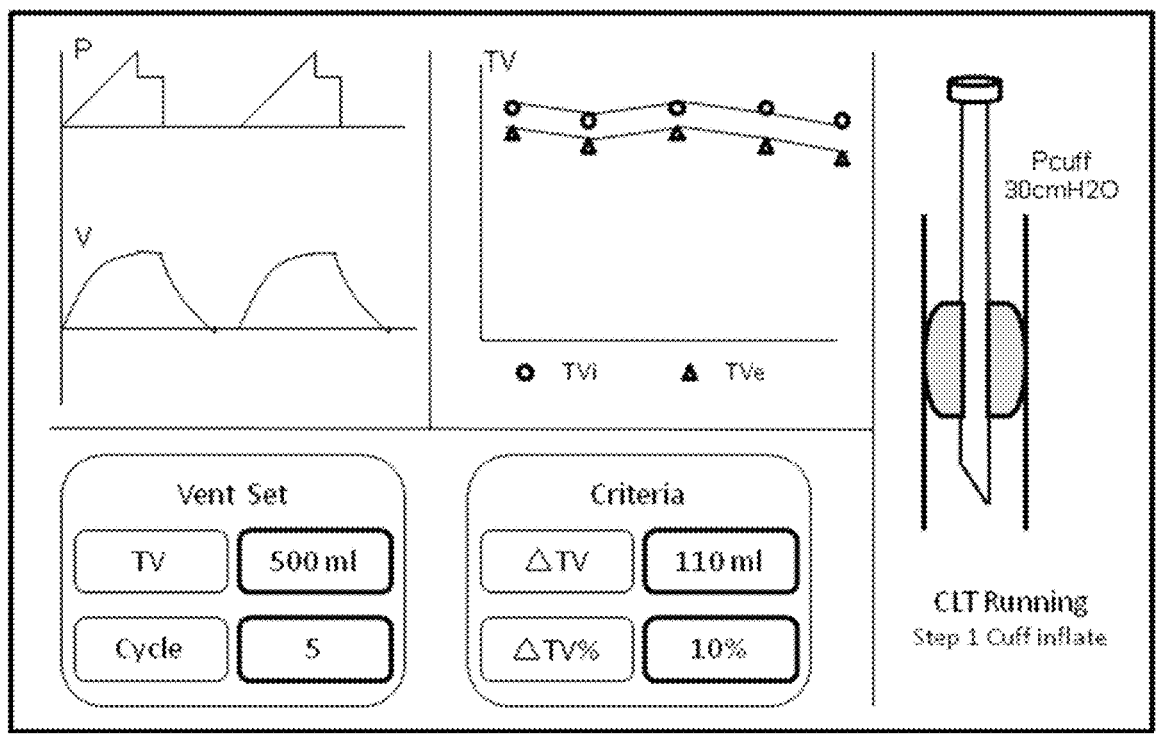
FIG. 3 is a schematic diagram of a GUI of a first stage where the cuff is inflated.

1. Ventilation parameters and an evaluation criterion used in the evaluation procedure: the ventilation parameters and the evaluation criterion are set before the evaluation procedure is started, the ventilation parameters include, for example, the tidal volume (TV), the number of cycles (Cycle) and the like, and the evaluation criterion is mainly represented by ΔTV and ΔTV %. As shown in FIG. 3, the preset tidal volume (TV) is 500 ml, the number of cycles (Cycle) is 5, ΔTV is 110 ml, and ΔTV % is 10%.

2. Parameters and image display during the evaluation: for example, the display of ventilation waveforms, the trend of key parameters, and the cuff pressure state image.

3. The final evaluation result: the evaluation result may be displayed using an image and/or text.

FIG. 3 shows a first stage where tidal volumes in several cycles are measured during the cuff inflation, and at the depicted moment, the cuff presents an inflated state in the graphs.

Figure 4:
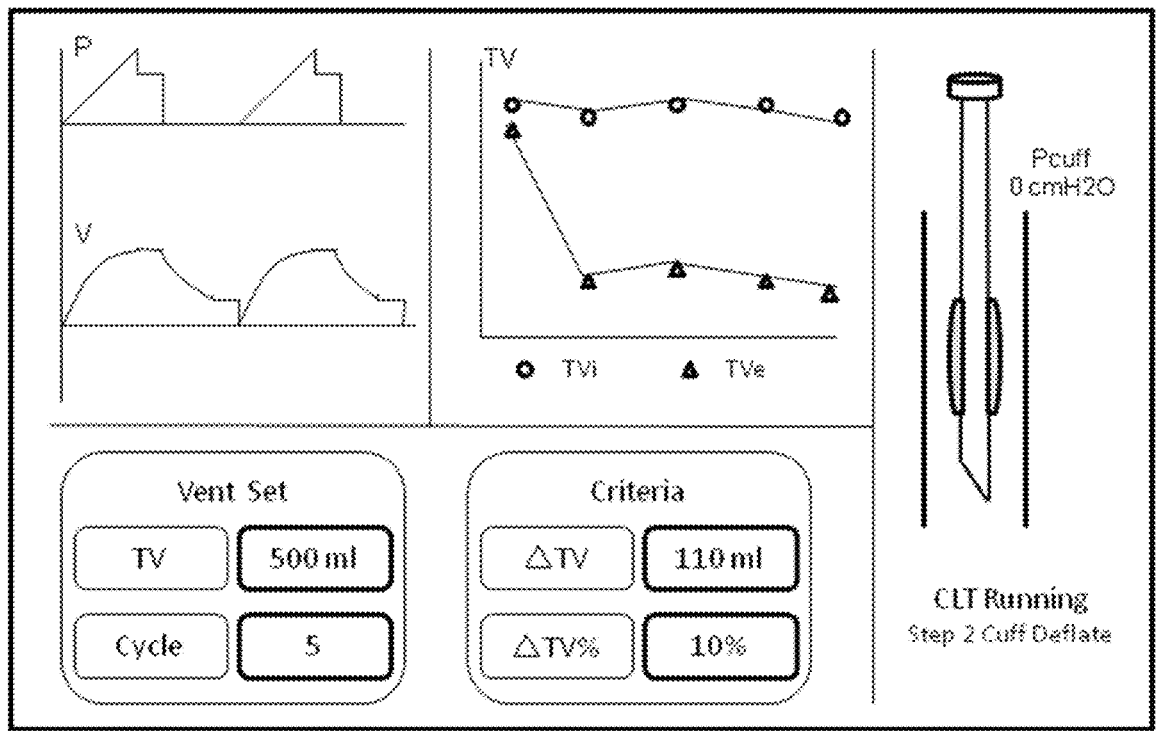
FIG. 4 is a schematic diagram of a GUI of a second stage where the cuff is deflated.

FIG. 4 shows a second stage where tidal volumes in several cycles are measured during the cuff deflation, and at the depicted moment, the cuff is completely deflated, the data processing unit changes the form of the cuff in the visualized graphs according to the cuff pressure, and the cuff turns to be in a collapsed state.

Figure 5:
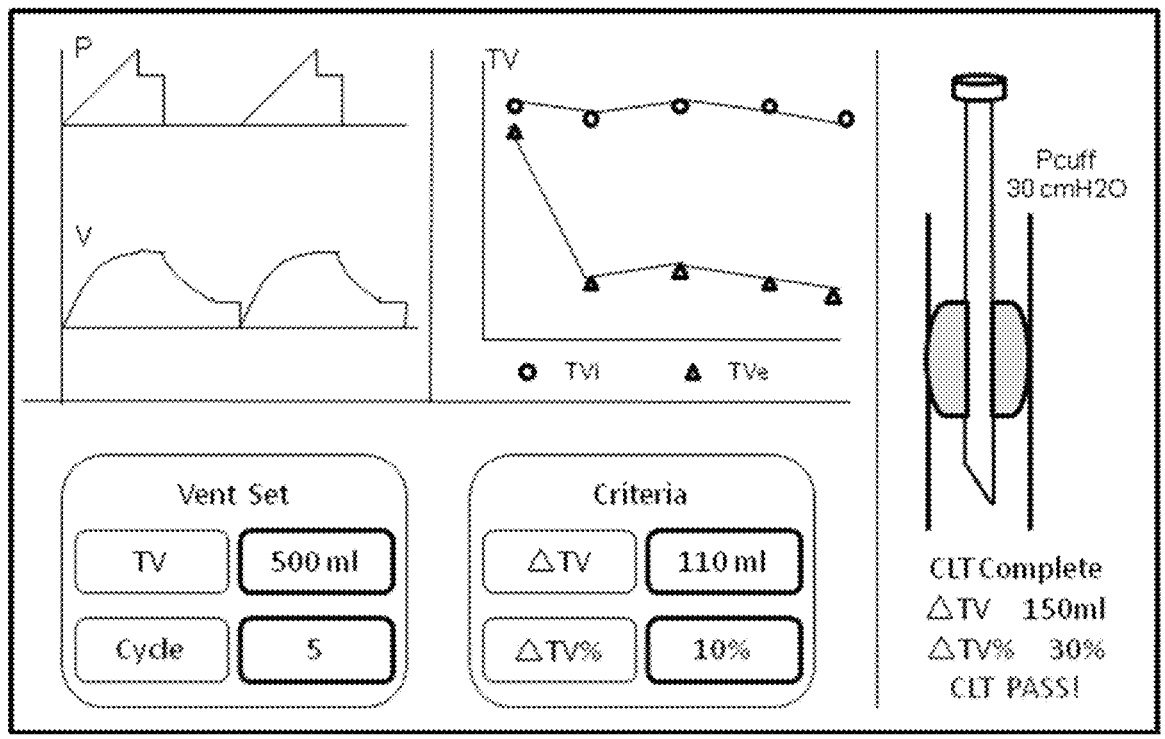
FIG. 5 is a schematic diagram of a GUI that a preset evaluation criterion is met.

FIG. 5 shows that the test is finished, the preset evaluation criterion is met, the data processing unit changes the form of the cuff in the visualized graphs according to the evaluation result, such that the cuff presents an inflated state in the graphs, and the airway is in a normal shape, representing that the cuff leak test passes and indicating that extubation may be performed.

Figure 6:
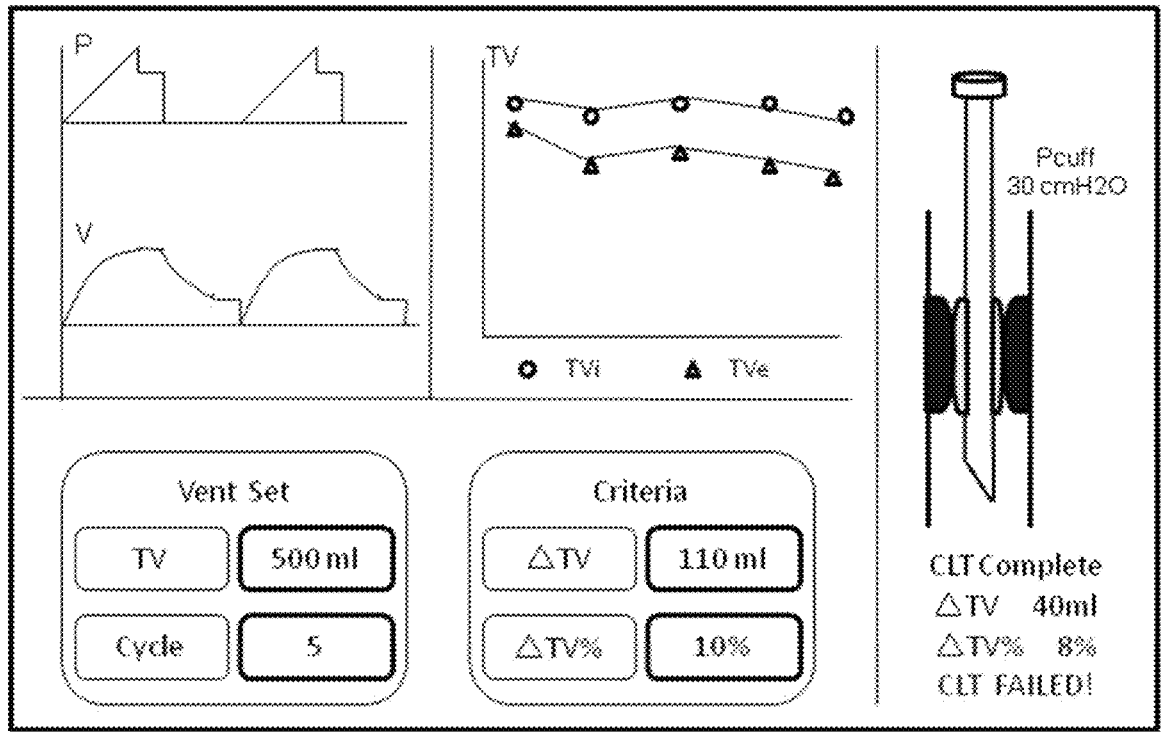
FIG. 6 is a schematic diagram of a GUI that the preset evaluation criterion is not met.

FIG. 6 shows that the test is finished, the preset evaluation criterion is not met, the data processing unit changes the forms of the cuff and the airway in the visualized graphs according to the evaluation result, such that the airway has local form change in the graphs, and the cuff presents a collapsed state, representing that the cuff leak test fails and the airway is narrow and indicating that the extubation may not be performed.

In this embodiment, text information is further displayed near the visualized graphs at the same time to prompt the evaluation result.

In other embodiments, different forms of airway or position relationships between the cuff and the airway may be used to represent different airway evaluation results.

Figure 7:
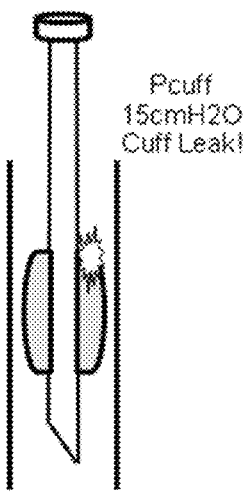
FIG. 7 is a schematic diagram of a GUI that the cuff is in a leaking state.

When the cuff is broken, the data processing unit changes the form of the cuff in the visualized graphs according to a detection result, such that the cuff present a leaking state in the graphs, for example, the graphs as shown in FIG. 7 represent that the cuff is broken.

Figure 8:
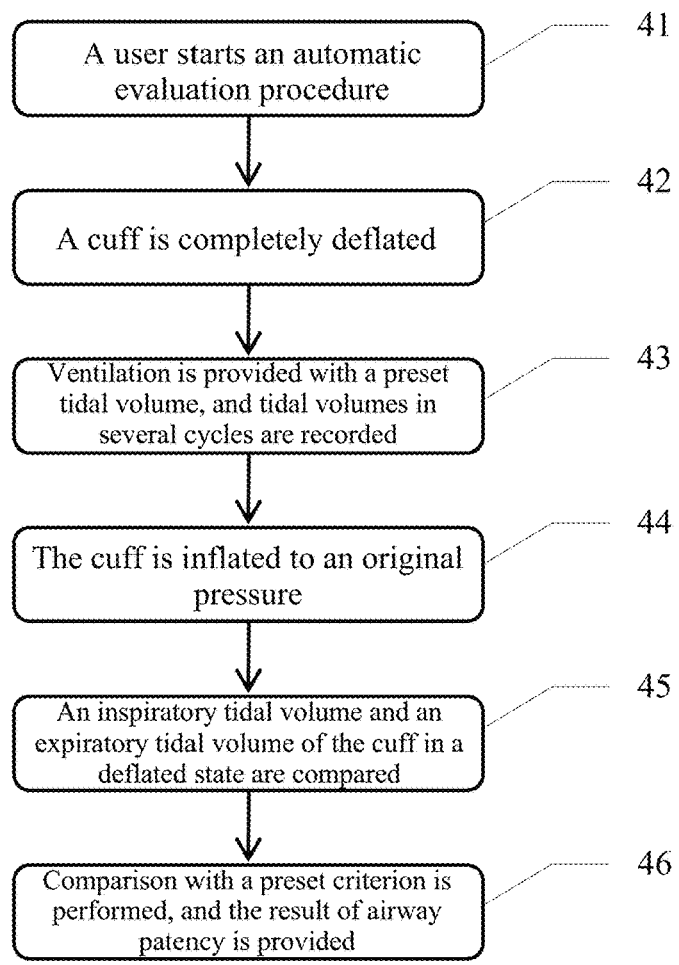
FIG. 8 is a schematic flowchart of an airway status evaluation method using respiration parameters detected after cuff deflation.

FIG. 8 shows an evaluation procedure according to the evaluation standard in which the respiration parameters detected after the cuff is completely deflated are compared to make a determination, including the following steps:

In step 41, the airway status evaluation procedure is started based on an instruction from a medical person. When the tracheal tube is in a normal ventilation mode, the inflation/deflation unit is controlled to maintain the cuff at the predetermined pressure, and a medical person starts an automatic evaluation procedure or may preset setting parameters such as the preset tidal volume and a quantity of ventilation cycles on a human-computer interface of the display unit.

In step 42, the inflation/deflation unit is controlled to completely deflate the cuff.

In step 43, the inspiratory tidal volume and the expiratory tidal volume after deflation are recorded, and at the same time the respiration unit is controlled to provide mechanical ventilation for a patient with the preset tidal volume. When the respiration monitoring unit is a flow sensor, the flow sensor monitors the respiratory flow rate of the patient in real time, and the data processing unit may calculate the inspiratory tidal volume and the expiratory tidal volume according to the respiratory flow rate. The inhalation parameter and the exhalation parameter are values measured in one respiratory cycle or average values measured in multiple respiratory cycles.

In step 44, the inflation/deflation unit is controlled to inflate the cuff to the preset pressure.

In step 45, the inspiratory tidal volume and the expiratory tidal volume after deflation are compared. The comparison result may be the difference, ratio, percentage or the like between the inspiratory tidal volume and the expiratory tidal volume.

In step 46, the comparison result is compared with the preset criterion to obtain the evaluation result of airway patency and output the evaluation result.

In this embodiment, the tidal volume may also be replaced with any one of the respiratory flow rate, airway pressure, carbon dioxide content and chemical indicator content, and the airway status of a patient may be evaluated likewise by the foregoing evaluation procedure.

In this embodiment, after a medical person starts an airway status evaluation procedure, the inflation and deflation of the cuff are implemented in a full-automatic control manner, the respiration parameters may be automatically monitored, and the evaluation result may be automatically calculated, without requiring a medical person to operate the cuff and the ventilator or to evaluate the airway status according to the observation for the patient, thereby automatically evaluating the airway status of the patient. In one evaluation result output method, the evaluation result is displayed in a visualized graphical representation manner on a human-computer interaction interface to facilitate observation by a medical person.

In another embodiment, the cuff is inflated and deflated in a semi-automatic manner. The inflation/deflation unit is not connected to an inflation/deflation control unit, the inflation/deflation unit is manually inflated and deflated, the inflation/deflation control unit is electrically connected to the signal output end of the pressure sensor, and after a medical person starts an airway status evaluation procedure, when it is needed to deflate the cuff, the inflation/deflation control unit outputs prompt information about deflating the cuff, and medical personnel manually operates the inflation/deflation unit (e.g., a syringe, a proportional valve, or an air evacuation valve) to deflate the cuff. When the detection of the respiration parameters used for evaluation is completed, the inflation/deflation control unit outputs prompt information about inflating the cuff, medical personnel manually operates the inflation/deflation unit to inflate the cuff, the pressure sensor detects the cuff pressure in real time and feeds back same to the inflation/deflation control unit, and when the cuff is inflated to the preset pressure, the inflation/deflation control unit outputs prompt information about stopping inflation.

The airway status evaluation apparatuses described above may be manufactured into independent products, and implements human-computer information exchanged on the display unit thereof, and in a further embodiment, the airway status evaluation apparatus may share some components with a ventilator, which will be explained below.

Figure 9:
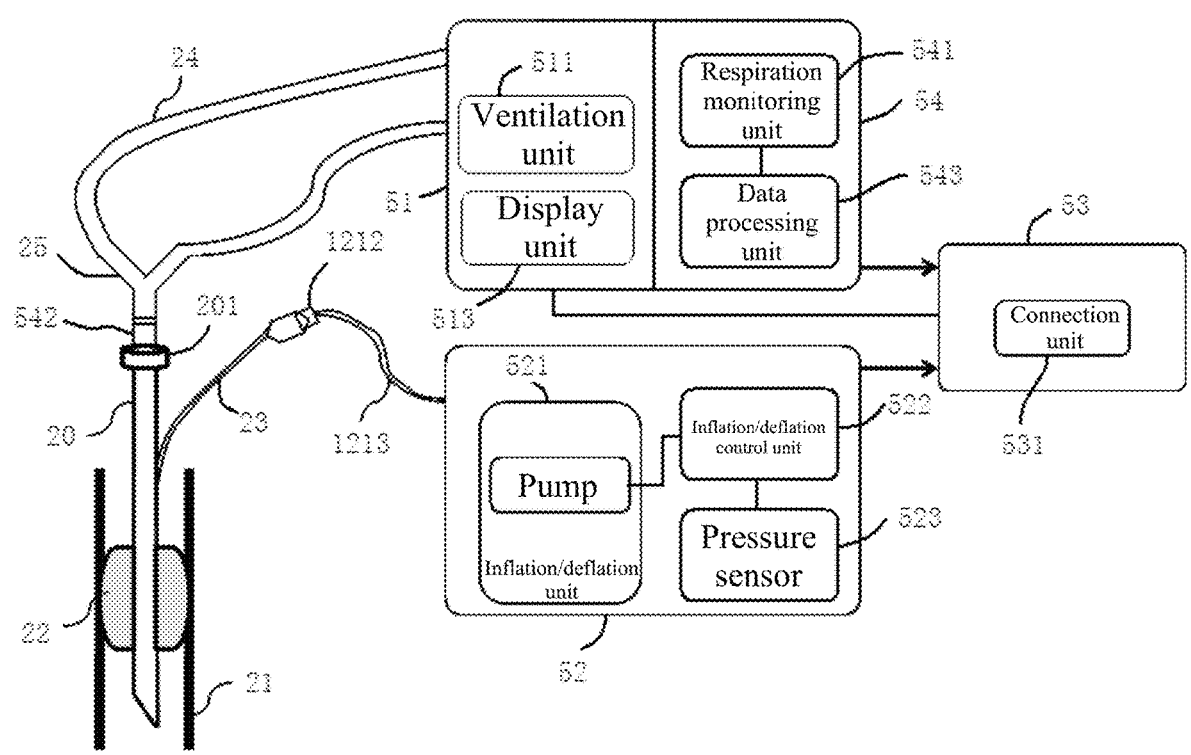
FIG. 9 is a schematic structural diagram of an airway status evaluation apparatus according to some embodiments.

As shown in FIG. 9, a ventilator may include a breathing circuit 24, a Y-shaped member 25, a respiration unit 511 and a display unit 513, the respiration unit 511 being connected to the breathing circuit 24, and an inspiration conduit and an expiration conduit of the breathing circuit 24 being respectively connected to a first and a second end of the Y-shaped member 25. An airway status evaluation apparatus includes three units. A first unit 54 includes a respiration monitoring unit 541, a connection joint 542 and a data processing unit 543, the respiration monitoring unit 541 being disposed in the connection joint 542. When in use, the connection joint 542 is connected between a third end of the Y-shaped member 25 and an exposed end 201 of a catheter 20, such that the respiration monitoring unit 541 may be connected to the breathing circuit 24 to monitor respiration parameters of a patient. A second unit 52 includes an inflation/deflation unit 521, an inflation/deflation control unit 522 and a pressure sensor 523, which are the same as those disclosed above and will not be described again in detail herein. A third unit is a connection unit 53, and the connection unit 53 is used to be in signal connection with the ventilator 51. For example, the connection unit 53 may be a wireless communication unit, and performs data interaction with the ventilator in a wireless communication manner. As another example, the connection unit 53 may also be a connector for electrical contact through a conductor, and the airway status evaluation apparatus may be designed as a plug-in unit electrically connected to the ventilator by means of point contact or a pin connector, so as to receive an instruction from the ventilator and/or upload detection or calculation data to the ventilator.

The evaluation result and the graphic data displaying a visualized graph of a pharynx of the patient inserted by the tracheal tube obtained by the data processing unit 543 may be output to the ventilator and displayed on the display unit 531 of the ventilator, such that the airway status evaluation apparatus and the ventilator share the display unit.

In one embodiment, the airway status evaluation apparatus directly uses the respiration monitoring unit in the ventilator, rather than including a respiration monitoring unit and a connection joint, such that the airway status evaluation apparatus may serve as a part or as a plug-in unit of the ventilator.

Figure 10:
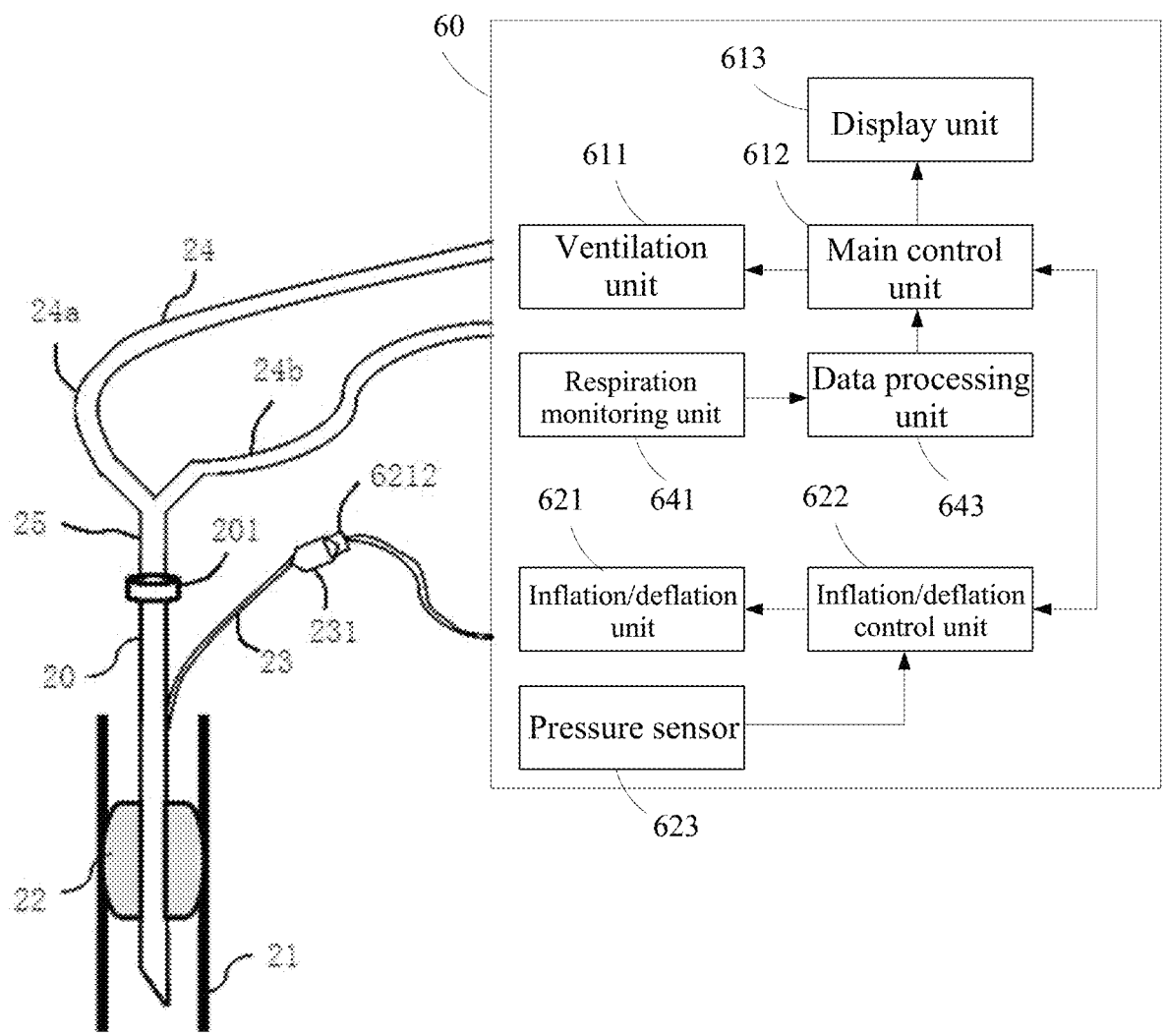
FIG. 10 is a schematic structural diagram of an airway status evaluation apparatus according to some embodiments.

Referring to FIG. 10, a catheter 20 of a tracheal tube is inserted into the airway 21 of a patient in a normal working state, a cuff 22 is fixed outside an end of the catheter 20 extending into the airway 21, one end of an inflation tube 23 is connected to the inside of the cuff 22, and the other end thereof is exposed and is connected to an air source. An exposed end 201 of the catheter 20 is connected to a breathing circuit of a ventilator 24.

The ventilator 60 includes the breathing circuit 24, a respiration unit 611, a main control unit 612, a display unit 613, a respiration monitoring unit 641 and the airway status evaluation apparatus, and the airway status evaluation apparatus includes a data processing unit 643, an inflation/deflation unit 621, an inflation/deflation control unit 622 and a pressure sensor 623.

The breathing circuit 24, the respiration unit 611, the respiration monitoring unit 641, the data processing unit 643, the inflation/deflation unit 621, the inflation/deflation control unit 622 and the pressure sensor 623 are the same as those in the foregoing embodiments and will not be described again in detail herein.

The main control unit 612 is used for the operation control and data processing (for example, calculation and processing respiration parameters) of the ventilator. In this embodiment, the main control unit 612 is electrically connected to the respiration unit 611, the main control unit 612 controls the opening/closing and the opening degree of an inhalation valve and an exhalation valve based on an instruction from a user or the default settings, such that a specific air flow is output to the lung of the patient through the breathing circuit 24 and the catheter 20, and the airway pressure and the tidal volume are maintained at specific levels, so as to implement mechanical ventilation for the patient. The main control unit 612 is electrically connected to the display unit 613, outputs display data to the display unit 613, and receives an operation instruction from the display unit. The main control unit 612 is further respectively electrically connected to the data processing unit 643 and the inflation/deflation control unit 622, receives the evaluation result and other data from the data processing unit 643, and outputs an inflation/deflation instruction to the inflation/deflation control unit 622, and then the inflation/deflation control unit 622 controls the action of the inflation/deflation unit 621 according to the inflation/deflation instruction.

The data processing unit 643, the inflation/deflation unit 621, the inflation/deflation control unit 622 and the pressure sensor 623 may be fabricated into one independent an airway status evaluation apparatus plug-in unit, and the ventilator is provided with a plug port matching the airway status evaluation apparatus plug-in unit, such that when it is needed to automatically evaluate the airway status of the patient, the plug-in unit is plugged into the ventilator, and a first interface 6212 of the inflation/deflation unit 621 is connected to a second interface 231 of an exposed end of the inflation tube 23, and when not in use, the airway status evaluation apparatus plug-in unit may be removed from the ventilator.

In some embodiments, the data processing unit 643 and the main control unit 612 may be integrated into one unit, and in this case, an independent airway status evaluation apparatus plug-in unit includes the inflation/deflation unit 621, the inflation/deflation control unit 622 and the pressure sensor 623. In some embodiments, the inflation/deflation control unit 622 and the main control unit 612 may further be integrated into one unit, and in this case, the independent airway status evaluation apparatus plug-in unit only includes the inflation/deflation unit 621 and the pressure sensor 623.

In another embodiment, the airway status evaluation apparatus described above may further be integrated with a tracheal tube to form a tracheal intubation device.

In yet another embodiment, an airway status evaluation method is provided, including: receiving an airway status evaluation instruction from a user; measuring an exhalation parameter of a patient when the cuff of an air tube is respectively in an inflated state and in a deflated state; comparing the exhalation parameter values measured respectively in the inflated state and in the deflated state; and outputting an airway status evaluation prompt according to the comparison result.

Here, when the cuff is in an inflated state, the cuff is maintained at a predetermined pressure, and when the cuff is in a deflated state, the cuff is completely deflated. The exhalation parameter may be any one of a tidal volume, a respiratory flow rate, an airway pressure, a carbon dioxide content, and a chemical indicator content. The method for measuring the exhalation parameter values is also as described above. The method for obtaining the airway status by comparing the exhalation parameter values measured respectively in the inflated state and in the deflated state is as described above, which will not be described again.

In another embodiment, an airway status evaluation method is provided, including: receiving an airway status evaluation instruction from a user; measuring an inhalation parameter value and an exhalation parameter value of a patient when the cuff of the air tube is in a deflated state; comparing the measured inhalation parameter value and the measured exhalation parameter value; and outputting an airway status evaluation prompt according to the comparison result.

Here, when the cuff is in a deflated state, the cuff is completely deflated; the exhalation and inhalation parameters are any one of a tidal volume, a respiratory flow rate, an airway pressure, a carbon dioxide content, and a chemical indicator content; the method for measuring the inhalation and exhalation parameter values is also as described above; and the method for obtaining the airway status by comparing the measured inhalation parameter value and the measured exhalation parameter value is as described above, which will not be described again.

In another embodiment, an airway status evaluation apparatus is provided, including: a receiving unit to receive an airway status evaluation instruction from a user and output an evaluation trigger command; a respiration parameter detection unit connected to the interface unit, to measure exhalation parameters of a patient when the cuff of the air tube is respectively in an inflated state and in a deflated state after receiving the evaluation trigger command; a respiration parameter comparison unit, connected to the respiration parameter detection unit, to compare the exhalation parameter values measured respectively in the inflated state and in the deflated state; and an evaluation unit, connected to the respiration parameter comparison unit, to give a prompt to output an airway status evaluation prompt according to the comparison result.

Here, when the cuff is in an inflated state, the cuff is maintained at a predetermined pressure, and when the cuff is in a deflated state, the cuff is completely deflated; the exhalation parameter is any one of a tidal volume, a respiratory flow rate, an airway pressure, a carbon dioxide content, and a chemical indicator content; the method for measuring the exhalation parameter values is also as described above; and the method for obtaining the airway status by comparing the exhalation parameter values measured respectively in the inflated state and in the deflated state is as described above, which will not be described again.

In another embodiment, an airway status evaluation apparatus is provided, including: a receiving unit to receive an airway status evaluation instruction from a user and output an evaluation trigger command; a respiration parameter detection unit, connected to the interface unit, to measure an inhalation parameter value and an exhalation parameter value of a patient when the cuff of the air tube is in a deflated state after receiving the evaluation trigger command; a respiration parameter comparison unit, connected to the respiration parameter detection unit, to compare the measured inhalation parameter value and the measured exhalation parameter value; and an evaluation unit, connected to the respiration parameter comparison unit, to give a prompt to output an airway status evaluation prompt according to the comparison result.

Here, when the cuff is in a deflated state, the cuff is completely deflated; the exhalation and inhalation parameters are any one of a tidal volume, a respiratory flow rate, an airway pressure, a carbon dioxide content, and a chemical indicator content; the method for measuring the inhalation and exhalation parameter values is also as described above; and the method for obtaining the airway status by comparing the measured inhalation parameter value and the measured exhalation parameter value is as described above, which will not be described again.

The present disclosure is explained above using specific examples, which merely aid in the understanding of the present disclosure and are not intended to limit the present disclosure. For a person skilled in the art, changes may be made to the specific embodiments described above in accordance with the concept of the present disclosure.

The invention claimed is:

1. An apparatus for evaluating an airway status of a patient prior to extubation of a tracheal tube, the apparatus is a plug-in unit electrically connected to a ventilator, comprising:
an inflation/deflation unit comprising an interface connected to an inflation tube of the tracheal tube to inflate or deflate a cuff of the tracheal tube through the inflation tube;
a pressure sensor connected to the cuff to measure cuff pressure;
an inflation/deflation control unit, respectively connected to the inflation/deflation unit and a signal output end of the pressure sensor to control the inflation/deflation unit to inflate and deflate the cuff or to output prompt information about inflating or deflating the cuff such that the cuff is inflated to a predetermined pressure or completely deflated, and further electrically connected to the connection unit and communicating with the ventilator through the connection unit so as to receive an inflation/deflation instruction from the ventilator and/or feed back the cuff pressure to the ventilator;
a connection unit used to be in signal connection with the ventilator; and
a data processing unit electrically connected to a respiration monitoring unit which is used to monitor a respiration parameter of the patient;
after an automatic airway status evaluation procedure to evaluate an airway patency is started:
the inflation/deflation control unit is configured to automatically inflate and deflate the cuff, and
the data processing unit is configured to automatically: collect the respiration parameter of the patient from the respiration monitoring unit until the cuff is inflated and deflated to meet an evaluation state, evaluate the airway status of the patient according to the collected respiration parameter to obtain an evaluation result of the airway patency, and output the evaluation result to indicate whether the extubation can be performed.

2. The apparatus of claim 1, wherein the inflation/deflation control unit controls the inflation/deflation unit to maintain the cuff to be at the predetermined pressure when the tracheal tube is in a normal ventilation mode, controls the inflation/deflation unit to completely deflate the cuff that is at the predetermined pressure after the automatic airway status evaluation procedure is started, and controls the inflation/deflation unit to inflate the cuff again to the predetermined pressure after the automatic airway status evaluation procedure is finished.

3. The apparatus of claim 1, wherein the inflation/deflation unit comprises an inflation/deflation device and a first interface, the inflation/deflation device is an air pump, a syringe, a proportional valve or an air evacuation valve, a power component of the inflation/deflation device is electrically connected to the inflation/deflation control unit, an air input/output port of the inflation/deflation device is connected to the first interface, and the first interface is connected to the inflation tube of the cuff.

4. The apparatus of claim 1, wherein the connection unit is a wireless communication unit or a connector for electrical contact through a conductor.

5. The apparatus of claim 1, wherein the tracheal tube comprises a catheter, the cuff surrounding an outer face of an end of the catheter, and the inflation tube having one end connected to an inside of the cuff, and another end used to introduce air to the cuff.

6. A ventilator, comprising:
a breathing circuit, connected to an exposed end of a catheter of a tracheal tube, to provide a passage for a patient to inhale or exhale gas;
a respiration unit for providing mechanical ventilation for the patient, the respiration unit being connected to the breathing circuit;
a respiration monitoring unit connected to the breathing circuit to monitor a respiration parameter of the patient;
an inflation/deflation unit, comprising an interface connected to an inflation tube of the tracheal tube to inflate or deflate a cuff of the tracheal tube through the inflation tube;
an inflation/deflation control unit, connected to the inflation/deflation unit, to control the inflation/deflation unit to inflate and deflate the cuff so as to enable the cuff to meet an evaluation state; and
a data processing unit electrically connected to the respiration monitoring unit;

after an automatic airway status evaluation procedure to evaluate an airway patency is started:
the inflation/deflation control unit is configured to automatically inflate and deflate the cuff, and
the data processing unit is configured to automatically: collect the respiration parameter of the patient from the respiration monitoring unit when the cuff is inflated and deflated to meet the evaluation state, evaluate an airway status of the patient according to the respiration parameter to obtain an evaluation result of the airway patency prior to extubation of the tracheal tube, and output the evaluation result to indicate whether the extubation can be performed.

7. The ventilator of claim 6, wherein the ventilator further comprises a pressure sensor, connected to the cuff, and a signal output end of the pressure sensor is electrically connected to the inflation/deflation control unit.

8. The ventilator of claim 6, wherein the respiration parameter monitored comprises any one of a tidal volume, a respiratory flow rate, an airway pressure, a carbon dioxide content, and a chemical indicator content.

9. The apparatus of claim 1, wherein the data processing unit generates graphic data displaying a visual representation of a pharynx of the patient with the tracheal tube inserted and outputs the graphic data to the ventilator, wherein the graphic data is changed according to different evaluation results of the airway status, and the changed graphic data in the visual representation include at least one of a cuff state, an airway state, and a position relationship between the cuff and the airway, such that:
in a first stage of a cuff leak test in which tidal volumes are measured in multiple cycles during cuff inflation, the visual representation is changed to depict the cuff in an inflated state;
in a second stage of the cuff leak test in which tidal volumes are measured in multiple cycles during cuff deflation, the visual representation is changed to depict the cuff in a deflated state; and
in a third stage of the cuff leak test, if at least one preset evaluation criterion is met, the visual representation is changed to depict the cuff in the inflated state indicating that the extubation may be performed, or, if the at least one preset evaluation criterion is not met, the visual representation is changed to depict the cuff in a collapsed state and/or that the airway is narrow indicating that the extubation may not be performed.

* * * * *